United States Patent
Wu et al.

(10) Patent No.: US 6,323,361 B1
(45) Date of Patent: Nov. 27, 2001

(54) PHOTOCURABLE HALOFLUORINATED ACRYLATES

(75) Inventors: Chengjiu Wu, Morristown; Baopei Xu, Lake Hiawatha; Jianhui Shan, High Bridge; James T. Yardley, Morristown, all of NJ (US)

(73) Assignee: Corning Inc., Corning, NY (US)

( * ) Notice: Subject to any disclaimer, the term of this patent is extended or adjusted under 35 U.S.C. 154(b) by 0 days.

(21) Appl. No.: 08/842,783

(22) Filed: Apr. 17, 1997

(51) Int. Cl.[7] ................................... C07C 69/52
(52) U.S. Cl. .............................................. 560/223
(58) Field of Search ............................... 560/223

(56) References Cited

U.S. PATENT DOCUMENTS 3,055,932   9/1962   Verbanic et al. .................. 260/486

FOREIGN PATENT DOCUMENTS 0 128 701 A1   12/1984   (EP) .
0 820 980 A1   1/1998   (EP) .

OTHER PUBLICATIONS

B.M. Monroe and W.K. Smothers, in Polymers for Lightwave and Integrated Optics, Technology and Applications, L.A. Hornak, ed., p 145, Dekker, 1992.

T. Kaino, in Polymers for Lightwave and Integrated Optaics, Technology and Applications, L.A. Hornak, ed., p1, Dekker, 1992.

S. Ando, T. Matsuda, and S. Sasaki, Chemtech, 1994—12, p. 20.

Primary Examiner—Paul J. Killos
(74) Attorney, Agent, or Firm—Nixon Peabody LLP

(57) ABSTRACT

This invention relates to a novel class of halofluorinated acrylates and more particularly to chlorofluorinated or bromofluorinated acrylates characterized by a chlorofluorinated or bromofluorinated alkylene moiety with acrylate functions at both terminals. These chlorofluorinated acrylates may be photocured in the presence of a photoinitiator into transparent polymers useful as optical waveguiding materials.

18 Claims, No Drawings

PHOTOCURABLE HALOFLUORINATED ACRYLATES

BACKGROUND OF THE INVENTION

This invention relates to a novel class of halofluorinated acrylates and more particularly to chlorofluorinated or bromofluorinated acrylates characterized by achlorofluorinated alkylene moiety with acrylate functions at both terminals. These chlorofluorinated or bromofluorinated acrylates may be photocured in the presence of a photoinitiator into transparent polymers useful as optical waveguiding materials.

The use of photocuring technology has grown rapidly within the last decade. Photocuring involves the radiation induced polymerization or crosslinking of monomers into a three dimensional network. The polymerization mechanism can be either radical or cationic. Radical initiated polymerization is the most common. Most commercial photocuring systems consist of multifunctional acrylate monomers and free radical photoinitiators. Photocuring has a number of adavantages including: a 100% conversion to a solid composition, short cycle times and limited space and capital requirements.

Photocuring technology has recently been applied in planar waveguide applications. See, B. M. Monroe and W. K. Smothers, in Polymers for Lightwave and Integrated Optics, Technology and Applications, L. A. Hornak, ed., p. 145, Dekker, 1992. In its simplest application, a photocurable composition is applied to a substrate and irradiated with light in a predetermined pattern to produce (the light transmissive) or waveguide portion on the substrate. Photocuring permits one to record fine patterns (<1 $\mu$m) directly with light. The refractive index difference between the substrate and the light transmissive portion of the substrate can be controlled by either regulating the photocurable composition or the developing conditions.

Because of the dramatic growth in the telecommunications industry there is a need to develop photocurable compositions for optical waveguide and interconnect applications. In order to be useful in these applications, the photocurable composition must be highly transparent at the working wavelength and possess low intrinsic absorption and scattering loss. Unfortunately, in the near-infrared region, among which the 1300 and the 1550 nm wavelengths are preferred for optical communications, conventional photocurable materials possess neither the required transparency or low intrinsic absorption loss.

The absorption loss in the near-infrared stems from the high harmonics of bond vibrations of the C—H bonds which comprise the basic molecules in conventional acrylate photopolymers. One way to shift the absorption bands to higher wavelength, is to replace most, if not all, of the hydrogen atoms in the conventional materials with heavier elements such as deuterium, fluorine, and chlorine. See, T. Kaino, in Polymers for Lightwave and Integrated Optics, Technology and Applications, L. A. Hornak, ed., p. 1, Dekker, 1992. The replacement of hydrogen atoms with fluorine atoms is the easiest of these methods. It is known in the art that optical loss at 1300 and 1550 nm can be significantly reduced by increasing the fluorine to hydrogen ratio in the polymer. It was recently reported that some perfluorinated polyimide polymers have very low absorption over the wavelengths used in optical communications. See, S. Ando, T. Matsuda, and 5. Sasaki, Chemtech, 1994-12, p.20. Unfortunately, these materials are not photocurable.

U.S. Pat. No. 5,274,174 discloses a new class of photocurable compositions comprised of certain fluorinated monomers such as diacrylates with perfluoro or perfluoropolyether chains which possess low intrinsic absorption loss. It is, therefore, possible to make low loss optical interconnects from a photocurable system include these materials.

Fluorine substitution in the polymer structure, however, also induces some other less desirable changes in the polymer's physical properties. One such change is the decrease in refractive index. For a highly fluorinated acrylate photopolymer, the refractive index decreases to the 1.32 region when the H/F mole ratio reaches 0.25. For optical interconnect applications, to avoid loss of light, it is important that the refractive index of the core of a planar waveguide approximate and preferably match that of the optical fiber (generally 1.45). Another problem with fluorine substitution in the polymer is the decrease of the surface energy of the resulting photopolymer film which results in its reduced adhesion to other materials like substrates.

It is also important to be abovel to precisely control and fine tune the refractive index of the photopolymer at the working wavelength in optical waveguide and interconnect applications. A desired index of refraction can be produced by mixing photocurable monomers with different refractive indices. Most photopolymers made from conventional photocurable monomers have refractive indices in the region of 1.45–1.55. Depending on the application, it is often desirable to lower a photopolymer's refractive index. One way to do this is to mix low refractive index fluorinated monomers with conventional hydrocarbon-based monomers. Unfortunately this is difficult to accomplish because of the incompatibility or insolubility of the different monomer systems. Thus, there is a need for photocurable compositions which: (i) possess low optical loss in the near-infrared region, (ii) possess a refractive index approaching traditional optical fibers; and (iii) are compatible with both conventional hydrocarbon-based and highly fluorinated monomers.

DESCRIPTION OF THE INVENTION

The photocurable monomer of the invention is a di-, tri- or tetra-acrylate which contains a chlorofluorinated or bromofluorinated alkylene chain and has the formula:

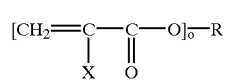

A wherein 0 in an integer of from 2–4; X is H, F, CH$_3$ or Cl and is preferably H, or Cl.

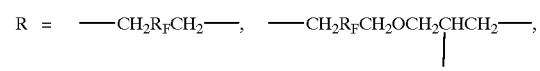

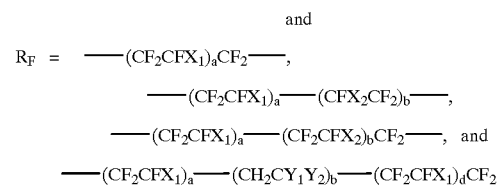

wherein X$_1$ is Cl or Br; X$_2$ is F, Cl or Br; Y$_1$ and Y$_2$ are the same or different and are H, CH$_3$, F, Cl or Br; and a, b, and c are the same or different and are integers of from 1–10 and preferably integers of from 1–7.

In the preferred embodiments, the above mentioned monomers contain chlorofluorinated or bromofluorinated alkylene chains which comprise chlorotrifluoroethylene or bromotrifluoroethylene repeating units and at least two terminal acrylate groups.

These monomers contain much less hydrogen than conventional photocurable monomers such that their inherent carbon-hydrogen bond absorption is greatly reduced. In addition, the introduction of chlorine or bromine atoms into the molecule offsets the effect of fluorine on the refractive index of the monomer producing a material with an index of refraction between about 1.40–1.48. As a result, the monomers of the invention are particularly useful in optical applications in the 1300–1550 nm wavelength region. The monomers are also compatible with both conventional hydrocarbon-based and highly fluorinated monomers. Because of this compatibility, it becomes possible to fine tune the refractive index and other physical properties of photocurable compositions containing these photocurable monomer.

In a second embodiment, the invention relates to a photocurable composition comprising at least one photocurable monomer of the invention and a photoinitiator.

In another embodiment, the invention relates to a process for producing an optical device containing a light transmissive region comprising:

a) applying a film of a photocurable composition comprising a photocurable monomer of the invention and a photoinitiator to a substrate; b) imagewise exposing said composition to sufficient actinic radiation to form exposed and unexposed areas on the substrate; and c) removing the unexposed portions of the composition.

In still another embodiment, the invention relates to an optical device comprising a light transmissive region wherein said light transmissive region comprises a photocurable composition of the invention.

In yet another embodiment, the invention relates to a process for the manufacture of an α,ω Diol of the formula:

$$HOCH_2—R_F—CH_2OH$$

comprising reacting a α,ω-Diester of the formula:

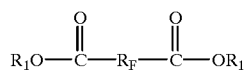

with aluminum hydride under conditions sufficient to produce said α,ω Diol.

In still another embodiment the invention relates to a process for the production of an α,ωdiol of the formula $HOCH_2—R_FCH_2OF$ which comprises reacting an α,ω-diester of the formula

with aluminum hydride under conditions sufficient to produce said α,ω-diol;
wherein
$R_1$ is a straight or branched chain alkyl group of from 1 to about 10 carbon atoms;

and

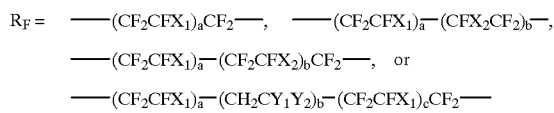

wherein $X_1$=Cl or Br; $X_2$=F, Cl, or Br; $Y_1$ and $Y_2$ are independently H, $CH_3$, F, Cl, or Br; a, b, and c are independently integers from 1 to about 10.

All of the photocurable monomers of the invention may be made by using or adapting methods known in the art. Methods for the preparation of certain α,ω-diols with chlorofluorinated backbones are known. See, B. Boutevin, A. Rousseau, and D. Bosc, Jour. Polym. Sci., Part A, Polym. Chem., 30, 1279, 1993; B. Boutevin, A. Rousseau, and D. Bosc, Fiber and Integrated Optics, 13, 309, 1994; and B. Boutevin and Y. Pietrasanta, European Polym. Jour., 12, p.231, 1976.

The photocurable monomers of the invention may be prepared by following the general reaction scheme outlined below wherein $R_F$, and X have the meanings set forth above and $R_1$ is a straight or branched chain alkyl group of from 1–10 and preferably 1–3 carbon atoms.

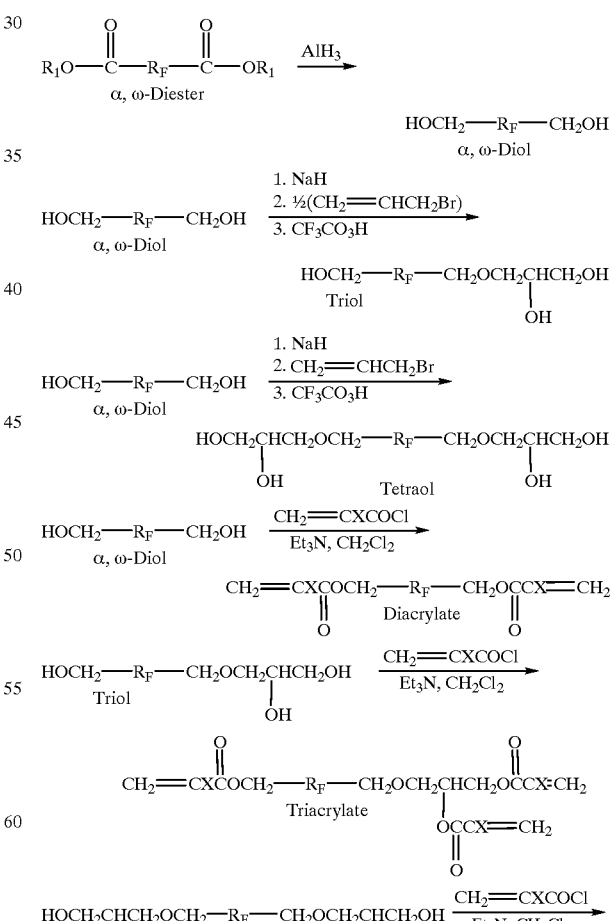

-continued

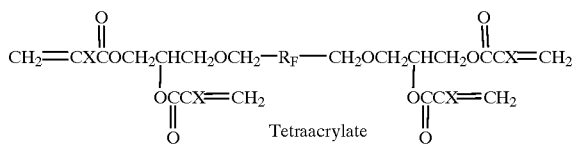
Tetraacrylate

Preparation of the α,ω-Diester.

Methods for the preparation of the α,ω-diester are known in the art. The diester may be prepared, for example by reducing with lithium aluminum hydride the appropriate telomer of a halotrifluoroethylene monomer. Examples of suitable halotrifluoroethylene monomers include: chlorotrifluoroethylene (or bromotrifluoroethylene), alone or mixture with other vinyl monomers such as bromotrifluoroethylene (or chlorotrifluoroethylene), tetrafluoroethylene, trifluoroethylene, vinylidene fluoride, vinyl fluoride, vinyl chloride, vinylidene chloride, ethylene, and propylene. Preparation of α,ω-diesters with a chlorofluorinated alkylene chain composed of chlorotrifluoroethylene monomer units is described in U.S. Pat. Nos. 2,806,865 and 2,806,866.

The prior art processes discussed above produce mixtures of α,ω-diols because of the partial reduction of chlorine and bromine in the α,ω-diester to hydrogen. Applicants have unexpectedly found that a pure (not a mixture) α,ω-diol can be obtained by using an aluminum hydride reducing agent. Compare Example 1 and Examples 2–4 below.

Preparation of Triols and Tetraols.

The α,ω-diols can be converted to triols and tetraols by methods known in the art. For example, a α,ω-triol can be obtained by: reacting the α,ω-diol with a metal hydroxide base or a metal alkoxide base to produce a metal salt of the α,ω-diol; reacting the metal salt with an allyl halide to produce an allyl ether of the α,ω-diol; and finally reacting the allyl ether with a peroxyacid to produce a α,ω-triol. See, Turri, S.; Scicchitano, M.; and Tonelli, C., Jour. Polymer Science: Part A: Polymer Chemistry, 1966, 44, p.3263.

Preparation of the Di-, Tri- and Tetra-acrylates.

The di-, tri-, and tetra-acrylates can also be prepared by methods known in the art. For example, a triacrylate of the invention may be prepared by reacting the triol described above with an acryloyl halide in the presence of an organic base and an anhydrous aprotic solvent.

In addition to the photocurable monomer described above, other photocurable compounds which are known in the art may be incorporated into the photocurable compositions of the invention. These compounds include monomers, oligomers and polymers containing at least one terminal ethylenically unsaturated group and being capable of forming a high molecular weight polymer by free radical initiated, chain propagating addition polymerization.

Suitable monomers include, but are not limited to, ethers, esters and partial esters of: acrylic and methacrylic acid; aromatic and aliphatic polyols containing from about 2 to about 30 carbon atoms; and cycloaliphatic polyols containing from about 5 to about 6 ring carbon atoms. Specific examples of compounds within these classes are: ethylene glycol diacrylate and dimethacrylate, diethylene glycol diacrylate and dimethacrylate, triethylene glycol diacrylate and dimethacrylate, hexane diacrylate and dimethacrylate, trimethylolpropane triacrylate and trimethacrylate, dipentaerythritol pentaacrylate, pentaerythritol triacrylate and trimethacrylate, alkoxylated bisphenol-A diacrylates and dimethacrylates (e.g, ethoxylated bisphenol-A di-acrylate and dimethacrylate), propoxylated bisphenol-A diacrylates and dimethacrylates, ethoxylated hexafluorobisphenol-A diacrylates and dimethacrylates and mixtures of the above compounds. Preferred monomers include multifunctional aryl acrylates and methacrylates. More preferred aryl acrylate monomers include di-, tri- and tetra-acrylates and methacrylates based on the bisphenol-A structure. Most preferred aryl acrylate monomers are alkoxylated bisphenol-A diacrylates and dimethacrylates such as ethoxylated bisphenol-A diacrylates and dimethacrylates, and ethoxylated hexafluorobisphenol-A diacrylates and dimethacrylates.

Suitable oligomers include, but are not limited to, epoxy acrylate oligomers, aliphatic and aromatic urethane acrylate oligomers, polyester acrylate oligomers, and acrylated acrylic oligomers. Epoxy acrylate oligomers (such as Ebercryl 600 by Radcure) are preferred.

Suitable polymers include, but are not limited to, acrylated polyvinyl alcohol, polyester acrylates and methacrylates, acrylated and methacrylated styrene-maleic acid copolymers. Acrylated styrene-maleic acid copolymers such as Sarbox SR-454 sold by Sartomer are preferred.

The photocurable component is comprised of photocurable monomer A, and optionally the other photocurable compounds described above. The photocurable component is present in an amount sufficient to photocure and provide image differentiation upon exposure to sufficient actinic radiation. The amount of the photocurable component in the photocurable composition may vary widely. Typically the photocurable component is present in an amount of from about 35 to about 99% by weight of the overall composition. In a preferred embodiment, the photocurable component is present in an amount of from about 80 to about 99% by weight and more preferably from about 95 to about 99% by weight in the overall composition. The weight ratio of monomer A to the other photocurable compounds may vary from about 1:9 to about 9:1. Preferably the weight ratio ranges from about 1:1 to about 9:1.

The photocurable composition further comprises at least one photoinitiator which photolytically generates activated species capable of inducing polymerization. Any photoinitiator known to be useful in the polymerization of acrylates or methacrylates may be used in the photocurable compositions of the invention. Suitable photoinitiators include aromatic ketone derivatives such as benzophenone, acrylated benzophenone, phenanthraquinone, 2,3-dichloronaphthoquinone, benzyl dimethyl ketal and other aromatic ketones (e.g. benzoin), benzoin ethers such as benzoin methyl ether, benzoin ethyl ether, benzoin isobutyl ether and benzoin phenyl ether. Preferred photoinitiators include 1-hydroxy-cyclohexyl-phenyl ketone (Irgacure 184), benzoin, benzoin ethyl ether, benzoin isopropyl ether, benzophenone, benzodimethyl ketal (Irgacure 651), α,α-diethyloxy acetophenone, α,α-dimethyloxy-α-hydroxyacetophenone (Darocur 1173), 1-[4-(2-hydroxyethoxy)phenyl]-2-hydroxy-2-methyl-propan-1-one (Darocur 2959), 2-methyl-1-[4-methylthio)phenyl]-2-morpholino-propan-1-one (Irgacure 907), 2-benzyl-2-dimethyl-1-(4-morpholinophenyl)-butan-1-one (Irgacure 369), poly{1-[4-(1-methylvinyl)phenyl]-2-hydroxy-2-methyl-propan-1-one} (Esacure KIP), [4-(4-methylphenylthio)-phenyl]-phenylmethanone (Quantacure BMS), and dicampherquinone. The most preferred photoinitiators are those which tend not to yellow upon irradiation. Such photoinitiators include benzodimethyl ketal (Irgacure 651), α,α-dimethyloxy-α-hydroxy acetophenone (Darocur 1173), 1-hydroxycyclohexyl-phenyl ketone (Irgacure 184), and 1-[4-(2-hydroxyethoxy)-phenyl]-2-hydroxy-2-methyl-propan-1-one (Darocur 2959).

The photoinitiator is present in an amount sufficient to effect photopolymerization of the photocurable compound upon exposure to sufficient actinic radiation. The photoinitiator may comprise from about 0.01 to about 10% by weight preferably from about 0.1 to about 6% by weight and most preferably from about 0.5 to about 4% by weight based upon the total weight of the photocurable composition.

Various optional additives may also be added to the photocurable compositions of the invention depending upon the application in which such they are to be used. Examples of these optional additives include antioxidants, photostabilizers, volume expanders, fillers (e.g., silica and glass spheres), dyes, free radical scavengers, contrast enhancers and UV absorbers. Antioxidants include such compounds as phenols and particularly hindered phenols including Irganox 1010 from Ciba-Geigy; sulfides; organoboron compounds; organophosphorous compounds; and N,N'-hexamethylenebis(3,5-di-ter(-butyl-4-hydroxyhydrocinnamamide) available from Ciba-Geigy under the tradename Irganox 1098. Photostabilizers and more particularly hindered amine light stabilizers include, but are not limited to, poly[(6-hexamethylene [2,2,6,6,-tetramethyl-4-piperidyl)imino)] available from Cytec Industries under the tradename Cyasorb UV3346. Volume expanding compounds include such materials as the spiral monomers known as Bailey's monomer. Suitable dyes include methylene green, methylene blue, and the like. Suitable free radical scavengers include oxygen, hindered amine light stabilizers, hindered phenols, and 2,2,6,6-tetramethyl-1-piperidinyloxy free radical (TEMPO). Suitable contrast enhancers include other free radical scavengers. UV absorbers include benzotriazoles and hydroxybenzophenone. These additives may be included in quantities, based upon the total weight of the composition, of from about 0 to about 6%, and preferably from about 0.1% to about 1%. Preferably all components of the photocurable composition are in admixture with one another and more preferably in a substantially uniform admixture.

The photocurable compositions of this invention can be used in the formation of the light transmissive element of an optical device. Illustrative of such devices are planar optical slab waveguides, channel optical waveguides, ribbed waveguides, optical couplers, and splitters. The photocurable composition of this invention can also be used in the formation of negative working photoresists and other lithographic elements such as printing plates. In a preferred embodiment of the invention, the photocurable composition is used for producing a waveguide comprising a substrate containing a light transmissive element. Such waveguides are formed by applying a film of the photocurable composition of the invention to the surface of a suitable substrate. The film may be formed by any method known in the art, such as spin coating, dip coating, slot coating, roller coating, doctor blading, and evaporation.

The substrate may be any material on which it is desired to establish a waveguide including semiconductor materials such as silicon, silicon oxide and gallium arsenide. In the event that the light transmissive region on the substrate is to be made from a photocurable material which has an index of refraction which is lower than that of the substrate, an intermediate buffer layer possessing an index of refraction which is lower than the substrate must be applied to the substrate before the photocurable composition is added. Otherwise, the light loss in the waveguide will be unacceptable. Suitable buffers are made from semiconductor oxides, lower refractive index polymers or spin-on silicon dioxide glass materials.

Once a film of the photocurable composition is applied to the substrate, actinic radiation is directed onto the film in order to delineate the light transmissive region. That is, the position and dimensions of the light transmissive device are determined by the pattern of the actinic radiation upon the surface of the film on the substrate. The photopolymers of the invention are conventionally prepared by exposing the photocurable composition to sufficient actinic radiation. For purposes of this invention, "sufficient actinic radiation" means light energy of the required wavelength, intensity and duration to produce the desired degree of polymerize action in the photocurable composition. Suitable sources of actinic radiation include light in the visible, ultraviolet or infrared regions of the spectrum, as well as electron beam, ion or neutron beam or X-ray radiation. Actinic radiation may be in the form of incoherent light or coherent light such as light from a laser.

Sources of actinic light, exposure procedures, times, wavelengths and intensities may vary widely depending on the desired degree of polymerization, the index of refraction of the photopolymer and other factors known to those of ordinary skill in the art. The selection and optimization of these factors are well known to those skilled in the art.

It is preferred that the photochemical excitation be carried out with relatively short wavelengths (or high energy) radiation so that exposure to radiation normally encountered before processing (e.g., room lights) will not prematurely polymerize the polymerizable material. The energy necessary to polymerize the photocurable compositions of the invention generally ranges from about 5 mW/cm$^2$ to about 100 mW/cm$^2$ with typical exposure times ranging from about 0.1 second to about 5 minutes.

After the photocurable composition has been polymerized to form a predetermined pattern on the surface of the substrate, the pattern is then developed to remove the nonimage areas. Any conventional development method can be used such as flushing the unirradiated composition with a solvent. Suitable solvents include polar solvents, such as alcohols and ketones. The most preferred solvents are acetone, methanol, tetrahydrofuran and ethyl acetate.

The following non-limiting examples serve to illustrate the invention.

EXAMPLE 1

Preparation and Reduction of $CH_3OC(O)(CF_2CFCl)_2CF_2CO_2CH_3$ α,ω-diester by aluminum hydride A. rearation of $CH_3OC(O)(CF_2CFCl)_2CF_2CO_2CH_3$ To 225 parts of $CCl_3(CF_2CFCl)_3Br$ was added 290 parts of fuming sulfuric acid containing 50% sulfur trioxide. The mixture was stirred and heated gradually from room temperature to 170° C. The mixture was maintained at that temperature for 6 hours and then cooled to 0° C. After this cooling, 240 parts of methanol was added dropwise to the mixture. The solution was then heated to 150° C. for 2 hours, cooled to room temperature and poured into 200 parts of ice-water. Then, the solution was extracted with ether after which the ether layer was evaporated ("ether workup"). The solution was next distilled to yield 133 parts of the dimethylester, $CH_3OC(O)(CF_2CFCl)_2CF_2COOCH_3$(81% yield) was obtained. The characterization results of this product are consistent with the indicated structure.

B. Reduction of $CH_3OC(O)(CF_2CFCl)_2CF_2CO_2CH_3$ to $HOCH_2(CF_2CFCl)_2CF_2CH_2OH$ with aluminum hydride A solution of 310 part of 1.04 M $LiAlH_4$ in tetrahydrofuran was stirred at 0° C. under nitrogen. To this solution was added slowly 17.8 parts of 100% sulfuric acid. The solution was stirred for an additional hour at room temperature. After settlement of the lithium sulfate precipitate, 240 parts of the clear supernatant solution of $AlH_3$ (0.91M) was collected. To this 240 parts of AlH$_3$ solution which was stirred at 0° C. was slowly added a solution of 33.7 parts of the above prepared diester in 450 parts of tetrahydrofuran. The mole ratio of AlH$_3$ to CH$_3$OC(O)(CF$_2$CFCl)$_2$CF$_2$CO$_2$CH$_3$ was 2.6:1. After one hour, the excess hydride was carefully hydrolyzed with 20 parts of a 1:1 mixture of tetrahydrofuran and water. After ether workup and distillation, 28 parts of the diol, HOCH$_2$(CF$_2$CFCl)$_2$CF$_2$CH$_2$OH, was obtained (quantitative). The characterization results of this product are consistent with the indicated structure.

EXAMPLE 2

Reduction of CH$_3$OC(O)(CF$_2$CFCl)$_2$CF$_2$CO$_2$CH$_3$ α,ω-diester by lithium aluminum hydride A solution of 180 part of 1.04 M LiAlH$_4$ in tetrahydrofuran was stirred at 0° C. under nitrogen. To this solution was slowly added a solution of 30 parts of the diester CH$_3$OC(O)(CF$_2$CFCl)$_2$CF$_2$CO$_2$CH$_3$ in 450 parts of tetrahydrofuran. The mole ratio of LiAlH$_4$ to the diester was 2.6:1. After one hour, the excessive hydride was carefully hydrolyzed with 20 parts of a 1:1 mixture of tetrahydrofuran and water. After ether workup, 25 parts of crude product was obtained. GC-MS analysis identified this crude product as a mixture of 3 main products: the target diol in which only the ester groups were reduced, HOCH$_2$(CF$_2$CFCl)$_2$CF$_2$CH$_2$OH; HOCH$_2$CF$_2$CFHCF$_2$CFClCF$_2$CH$_2$OH diol in which one chlorine atom was reduced and HOCH$_2$(CF$_2$CFH)$_2$CF$_2$CH$_2$OH in which both chlorine atoms were reduced. The products were produced in a ratio of 60:35:5 respectively.

EXAMPLE 3

Reduction of CH$_3$OC(O)(CF$_2$CFCl)$_2$CF$_2$CO$_2$CH$_3$ α,ω-diester with lithium aluminum hydride-aluminum chloride complex A solution of 165 parts of 1.04 M LiAlH$_4$ in tetrahydrofuran was stirred at 0° C. under nitrogen. To this solution was slowly added 22 parts of anhydrous aluminum chloride. The mixture was stirred for one hour. A solution of 30 parts of the diester CH$_3$OC(O)(CF$_2$CFCl)$_2$CF$_2$CO$_2$CH$_3$ in 450 parts of tetrahydrofuran was then slowly added. The mole ratio of LiAlH4:AlCl$_3$:CH$_3$OC(O)(CF$_2$CFCl)$_2$CF$_2$CO$_2$CH$_3$ was 2.2:2.2:1 respectively. GC-MS analysis identified the presence of the chlorine reduced diol in the crude product.

EXAMPLE 4

Reduction of CH$_3$OC(O)(CF$_2$CFCl)$_2$CF$_2$CO$_2$CH$_3$ by sodium borohydride To a stirred solution of 30 parts of the diester CH$_3$OC(O)(CF$_2$CFCl)$_2$CF$_2$CO$_2$CH$_3$ in 450 parts of tetrahydrofran at 0° C. and under nitrogen, was slowly added 150 parts of 0.5M sodium borohydride in 2-methoxyethyl ether. The mole ratio of NaBH$_4$ to CH$_3$OC(O)(CF$_2$CFCl)$_2$CF$_2$CO$_2$CH$_3$ was 2.0:1. GC-MS analysis identified the presence of the chlorine reduced diol in the crude product.

The results from Examples 1–4 are described in Table 1 below.

TABLE 1

| Example: | EX. 1 | EX. 2 | EX. 3 | EX. 4 |
|---|---|---|---|---|
| Reducing agent (RA)* | AlH$_3$ | LiAlH$_4$ | LiAlH$_4$/AlCl$_3$ | NaBH$_4$ |
| Ratio RA:diester: | | | | |
| Theoretical | 1.5:1 | 2:1 | 2:1 | 2:1 |
| Actual | 2.6:1 | 2.5:1 | 2.2:1 | 2:1 |
| Reduction of chlorine | – | + | + | + |

*all runs were in THF, 0° C.

The results show that even when present in excess, aluminum hydride does not result in reduction of chlorine atoms in the reduced diol.

EXAMPLE 5

Preparation of CH$_2$=CHCO$_2$CH$_2$(CF$_2$CFCl)$_2$CF$_2$CH$_2$OC(O)CH=CH$_2$ diacrylate 80 parts of the diol prepared in Example 1 were mixed with 56.3 parts of triethylamine and 100 parts of methylene chloride and cooled to 0° C. To this solution was slowly added with stirring and under nitrogen 50 parts of freshly distilled acryloyl chloride in 100 parts of methylene chloride. After addition, the mixture was stirred for an additional 24 hours and the temperature was returned to ambient. The mixture was treated with water and worked up with ethyl ether. The crude product was purified by silica gel column chromatography (Merck #60) eluted with an ethyl acetate and hexane mixture. 28 parts of the purified diacrylate, CH$_2$=CHCO$_2$CH$_2$(CF$_2$CFCl)$_2$CF$_2$CH$_2$OC(O)CH=CH$_2$ was obtained. The characterization results are consistent with the indicated structure. $^{19}$F-NMR [δ (CF$_3$COOH), ppm]: 31.1 (2F), 35.5 (4F), and 53.6 (2F); $^1$H-NMR [δ, ppm]: 4.66 (t, 4H), 6.13 (ABX, 6H); Mass spectra: 454 (M$^+$, 0.35%), 452 (M$^+$, 0.57%), 426 ([M-CO or M-C$_2$H$_4$]$^+$, 0.42%), 424 ([M-CO or M-C$_2$H$_4$]$^+$, 0.63%), 383 ([M-CH$_2$=CHCO$_2$]$^+$, 0.21%), 381 ([M-CH$_2$=CHCO$_2$]$^+$, 0.31%), 85 ([CH$_2$=CHCO$_2$CH$_2$]$^+$, 5.13%), 55 ([CH$_2$=CHCO]$^+$, 100%); IR [film, cm$^{-1}$]: 2982 (w), 1747 (vs), 1637(m), 1412(vs), 1299(s), 1262(s), 11 65(vs), 1110 (s), 974(s), 806(m).

EXAMPLE 6

Preparation of CH$_2$=CClCO$_2$CH$_2$(CF$_2$CFCl)$_2$CF$_2$CH$_2$OC(O)CCl=CH$_2$ α, Cl-diacrylate The following materials were reacted according to the procedure set forth in Example 5 above: 44.5 parts of the diol prepared in Example 1, 31.3 parts of triethylamine, 14 parts of α-chloroacryloyl chloride and 100 parts of methylene chloride. 31 parts of CH$_2$=CClCO$_2$CH$_2$(CF$_2$CFCl)$_2$CF$_2$CH$_2$OC(O)CCl=CH$_2$ were obtained. The characterization results are consistent with the indicated structure.

EXAMPLE 7

Preparation of CH$_2$=CHCO$_2$CH$_2$(CF$_2$CFCl)$_4$CF$_2$CH$_2$OC(O)CCl=CH$_2$ diacrylate The following materials were reacted according to the procedure set forth in Example 5 above: 93 parts of HOCH$_2$(CF$_2$CFCl)$_3$CF$_2$CH$_2$OH, diol (prepared according to Example 1) 54 parts of triethylamine, 61 parts of acryloyl chloride and 250 parts of methylene chloride. 22 parts of pure $CH_2$=$CHCO_2CH_2(CF_2CFCl)_4CF_2CH_2OC(O)$ $CH$=$CH_2$ diacrylate were obtained. The characterization results are consistent with the indicated structure. $^{19}$F-NMR [δ ($CF_3COOH$), ppm]: 29.5~32.0(m. 6F), 36.0(s, 4F), 49.6~55.0(m, 4F); $^1$H-NMR [δ, ppm] 4.6(t, J=13.6 Hz, 4H), 6.1(ABX system, 6H); MS: 684 (M$^+$, 0.25), 576 ([$HOCH_2(CF_2CFCl)_4CF_2CH_2OH$]$^+$, 1.60), 460 ([$HOCH_2(CF_2CFCl)_3CF_2CH_2OH$]$^+$, 1.67), 433 ([$CH_2$=$CHCO_2CH_2(CF_2CFCl)_3$]$^+$), 344 ([$HOCH_2(CF_2CFCl)_2CF_2CH_2OH$]$^+$, 0.71), 317 ([$CH_2$=$CHCO_2CH_2(CF_2CFCl)_2$]$^+$, 0.24), 135 ([$CH_2$=$CHCO_2CH_2CF_2$]$^+$, 493), 85 ([$CH_2$=$CHCO_2CH_2$]$^+$, 7.13), 55 ([$CH_2$=$CHCO$]$^+$, 100); IR [film, cm$^{-1}$]: 2983(w), 1748(vs). 1637(m). 1411(s), 1261 (s), 1165(vs), 1122(vs), 971(vs), 806(s).

EXAMPLE 8

Preparation of [$CH_2$=$CHCO_2CH_2(CF_2CFCl)_2$—]$_2$ diacrylate

A. Preparation of $Cl_3CCF_2CFClCF_2CFClCFClCF_2CFClCF_2CCl_3$ (precursor of α,ω-diester)

A mixture of 86 parts of acetic anhydride, 105 parts of dichloromethane, 12.7 parts of granular zinc, and 81.8 parts of $Cl_3C(CF_2CFCl)_2$ Br were stirred at 45° C. for 2 hours. The unreacted zinc was removed from the mixture and 40 parts of water were added. The acetic anhydride was then hydrolyzed by the dropwise addition of 50 parts of 3N $H_2SO_4$ and the mixture was washed with aqueous sodium carbonate, worked up with ether and then distilled. 13.4 parts of the unreacted $Cl_3C(CF_2CFCl)_2Br$, and 44.1 parts of the residue, showed two GC peaks with a relative intensity of 1:6. The residue was then transferred into a quartz tube with 125 parts of 1,1,2-trichlorotrifluoroethane. Chlorine gas was bubbled through the mixture for 4 hours while the tube was irradiated with a U lamp at room temperature. After removal of solvent and fractional distillation, 44.5 parts of a single coupling product, $Cl_3CCF_2CFClCF_2CFClCFClCF_2CFClCF_2CCl_3$, was obtained. $^{19}$F-NMR (δ$_{CF3COOH}$,ppm): 17.3–29.2 (8F), 41.0–48.6 (4F).

B. Paration of $H_3CO_2C(CF_2CFCl)_2$—(CFCl $CF_2$)$_2CF_2CO_2CH_3$ α,ω-diester 44.5 parts of $Cl_3CCF_2CFClCF_2CFClCFClCF_2CFClCF_2CCl_3$, was reacted according to the procedure set forth in Example 1A above to yield 30 parts of $H_3CO_2C(CF_2CFCl)_2$—(CFCl $CF_2$)$_2CF_2CO_2CH_3$ α,ω-diester. Characterization results are consistant with the indicated structure.

C. Preparation of $HOCH_2(CF_2CFCl)_2$—(CFCl $CF_2$)$_2CF_2CH_2OH$ α,ω-diol 30 parts of $H_3CO_2C(CF_2CFCl)_2$—(CFCl $CF_2$)$_2CF_2CO_2CH_3$ were reacted according to the procedure set forth in Example 1B above to yield 26 parts of $HOCH_2(CF_2CFCl)_2$—(CFClCF$_2$)$_2CF_2CH_2OH$ α,ω-diol. The characterization results are consistant with the indicated structure.

D. Preparation of [$CH_2$=$CHCO_2CH_2(CF_2CFCl)_2$—]$_2$ diacrylate 13 parts of $HOCH_2(CF_2CFCl)_2$—(CFCl $CF_2$)$_2CF_2CH_2OH$ was reacted according to the procedure set forth in Example 5 above to yield 15 parts of [$CH_2$=$CHCO_2CH_2(CF_2CFCl)_2$—]$_2$ were obtained. The characterization results are consistant with the indicated structure.

EXAMPLE 9

Preparation of $HOCH_2CH(OH)CH_2OCH_2(CF_2CFCl)_3CF_2CH_2OCH_2CH(OH)CH_2OH$ α,ω-tetraol $HOCH_2(CF_2CFCl)_3CF_2CH_2OH$ diol was prepared according to the procedure outline in Example 1 above.

Then, to a stirred solution of 46.1 parts of the $HOCH_2(CF_2CFCl)_3CF_2CH_2OH$ diol in 200 parts of anhydrous t-butanol was slowly added at 0° C. a solution of 21.6 parts of potassium t-butoxide in 100 parts of t-butanol. After 2 hours, the temperature of the mixture was raised to 30° C. and 25 parts of allyl bromide was added. The mixture was stirred overnight. After filtration and vacuum removal of excess allyl bromide and most of the t-butanol, the residue was poured into 300 parts of water. After ether workup, 54 parts of diallyl product was obtained. $^{19}$F and $^1$H-NMR proved the completeness of the allylation.

54 parts of the diallyl product was then dissolved in 200 parts of methylene chloride and a mixture of 20 parts of triethylammonium trifluoroacetate with 10 parts of trifluoroacetic acid was added. To this chilled mixture was then added a trifluoroperoxyacetic acid solution (which was made by slowly adding 11 parts of 35% hydrogen peroxide to 25 parts of trifluoroacetic anhydride at 0° C.). The resulting mixture wax stirred for 2 hours. After 6 hours, the mixture was poured into ice-water. The organic layer was further washed with water and vacuum dried to yield 50 parts of $HOCH_2CH(OH)CH_2CH_2(CF_2CFCl)_3CF_2CH_2OH_2CH(OH)CH_2OH$ tetraol. The characterization results are consistant with the indicated structure.

EXAMPLE 10

Preparation of $CH_2$=$CHCO_2CH_2CH[OC(O)CH$=$CH_2]CH_2OCH_2(CF_2CFCl)_3CF_2CH_2OCH_2CH[OC(O)CH$=$CH_2]CH_2OOC(O)CH$=$CH_2$ tetracrylate 25 parts of $HOCH_2CH(OH)CH_2OCH_2(CF_2CFCl)_3CF_2CH_2OCH_2CH(OH)CH_2OH$ were reacted according to the procedure set forth in Example 5 above to yield 15 parts of $CH_2$=$CHCO_2CH_2CH[OC(O)CH$=$CH_2]CH_2OCH_2(CF_2CFCl)_3CF_2CH_2OCH_2CH[OC(O)CH$=$CH_2]CH_2OOC(O)CH$=$CH_2$. tetracrylate. The characterization results are consistant with the indicated structure.

EXAMPLE 11

Preparation of $CH_2$=$CClCO_2CH_2CH[OC(O)CCl$=$CH_2]CH_2OCH_2(CF_2CFCl)_3CF_2CH_2OCH_2CH[OC(O)CCl$=$CH_2]CH_2OOC(O)CCl$=$CH_2$ tetra-α-Cl-acrylate 25 parts of $HOCH_2CH(OH)CH_2OCH_2(CF_2CFCl)_3CF_2CH_2OCH_2CH(OH)CH_2OH$ were reacted according to the procedure set forth in Example 6 above to yield 12 parts of $CH_2$=$CClCO_2CH_2CH[OC(O)CCl$=$CH_2]CH_2OCH_2(CF_2CFCl)_3CF_2CH_2OCH_2CH[OC(O)CCl$=$CH_2]CH_2OOC(O)CCl$=$CH_2$. tetra-α-Cl-acrylate. The characterization results are consistant with the indicated structure.

EXAMPLE 12

Preparation of $CH_2$=$CHCO_2CH_2(CF_2CFCl)_3CF_2CH_2OCH_2CH[OC(O)CH$=$CH_2]CH_2OOC(O)CH$=$CH_2$triacrylate 25 parts of $HOCH_2(CF_2CFCl)_3CF_2CH_2OCH_2CH(OH)CH_2OH$ triol (prepared according to the procedure outlined in Example 9 above except that the amount of the diol starting material was doubled (92 parts)) were reacted according to the procedure set forth in Example 5 above to yield 10 parts of $CH_2$=$CHCO_2CH_2(CF_2CFCl)_3CF_2CH_2OCH_2CH[OC(O)CH$=$CH_2]CH_2$ $OOC(O)CH$=$CH_2$. triacrylate. The characterization results are consistant with the indicated structure.

EXAMPLE 13

Comparison of the Refractive Indices and Near-IR Absorption of Conventional Hydrocarbon-based Diacrylates, Highly Fluorinated Diacrylates and the Chlorofluorodiacrylates of the Invention The refractive indices and near-IR absorption of three diacrylate monomers are compared in Table 2 below:

TABLE 2

| | Index of Refraction* | Near IR Absorption** |
|---|---|---|
| $H_2C=CHCO_2CH_2(CF_2CFCl)_2CF_2CH_2OC(O)CH=CH_2$ | 1.4221 | lowest |
| $H_2C=CHCO_2CH_2(CF_2)_4CH_2OC(O)CH=CH_2$ | 1.3891 | medium |
| $H_2C=CHCO_2CH_2(CH_2)_4CH_2OC(O)CH=CH_2$ | 1.4560 | highest |

*measured using an Abbe refractometer at 589 nm
**relative comparison of the 1300 and the 1550 nm absorption of the three monomers in a 2 mm quartz cell This example demonstrates that the chlorofluoroacrylates of the invention have indices of refraction which approximate the indices of refraction of optical fibers making them more suitable for optical interconnect applications than the highly fluorinated diacrylates. The data also show that the diacrylates of the invention have lower IR absorption which makes them suitable for low loss optical applications.

EXAMPLES 14–22

General Procedure Used to Prepare the Photopolymers Described Below

The photocurable monomer(s) and photoinitiator used in the examples which follow were stirred at 30–50° C. in a brown glass container under nitrogen for 5–8 hours. The mixture was then pressure-filtered through a 0.2 micron PTFE membrane to obtain a homogeneous clear photocurable composition. The composition was spin-coated onto a silicon wafer or a quartz plate to form a 2–10 micron thick liquid layer. The plate was then irradiated under medium pressure mercury UV lamp in a nitrogen atmosphere for 0.1–60 seconds to obtain a tough solid coating.

EXAMPLE 14

Preparation of $H_2C=CHCO_2CH_2(CF_2CFCl)_2CF_2CH_2OC(O)CH=CH_2$ photopolymer

The monomer prepared in Example 5 above was mixed with 2.0 wt.% of α,α-dimethyloxy-α-hydroxyacetophenone (Darocur 1173) into a homogenous composition and photocured according to the procedure set forth above. The resulting product was a clear, tough, solid polymer film. The refractive indices of the monomer and the polymer are 1.4221 (at 589 nm) and 1.4586 (at 633 nm) respectively.

EXAMPLE 15

Preparation of $H_2C=CClCO_2CH_2(CF_2CFCl)_2CF_2CH_2OC(O)CCl=CH_2$ photopolymer

The monomer prepared in Example 6 above was mixed with 2.0 wt. % of benzodimethyl ketal (Irgacure 651) into a homogeneous composition and photocured according to the procedure set forth above. The resulting product was a clear, tough, solid polymer film.

EXAMPLE 16

Preparation of $H_2C=CHCO_2CH_2(CF_2CFCl)_4CF_2CH_2OC(O)CH=CH_2$ photopolymer

The monomer prepared in Example 7 above was mixed with 1 wt. % LR 8893 X (Ciba-Geigy) into a homogeneous composition and photocured according to the procedure set forth above. The resulting product was a clear, tough, solid polymer film. The refractive indices of the monomer and the polymer are 1.4232 (at 589 nm) and 1.4416 (at 810 nm) respectively.

EXAMPLE 17

Preparation of $[CH_2=CHCO_2CH_2(CF_2CFCl)_2-]_2$ photopolymer

The monomer prepared in Example 8 above was mixed with 1.5 wt % of benzodimethyl ketal (Irgacure 651) into a homogeneous composition and photocured according to the procedure set forth above. The resulting product was a clear, tough, solid polymer film. The refractive indices of the monomer and the polymer are 1.4482 (at 589 nm) and 1.4724 (at 633 nm) respectively.

EXAMPLE 18

Preparation of $CH_2=CHCO_2CH_2CH[OC(O)CH=CH_2]CH_2OCH_2(CF_2CFCl)_3CF_2CH_2OCH_2CH[OC(O)CH=CH_2]CH_2OOC(O)CH=CH_2$ tetracrylate The monomer produced in Example 10 was mixed with 1.5 wt % of benzodimethyl ketal (Irgacure 651) to produce a homogeneous composition. The composition was photocured according to the procedure set forth above. The resulting product was a clear, tough, solid polymer film.

EXAMPLE 19

Preparation of a mixture of $H_2C=CHCO_2CH_2(CF_2CFCl)_4CF_2CH_2OC(O)CH=CH_2$ (A) and $H_2C=CClCO_2CH_2(CF_2CFCl)_4CF_2CH_2OC(O)CCl=CH_2$ (B)

Monomers A and B were mixed together in three weight ratios: 10.3/89.7; 32.6/67.4; and 49.4/50.6 and each of the resulting mixtures was combined with 1 wt. % of LR 8893 X as photoinitiator. Each composition was photocured according to the procedure set forth above. The refractive indices of resulting photocurable compositions and the photocured polymers made from these compositions are listed in Table 3 below:

TABLE 3

| Ratio of monomers in photocurable composition (A/B) | Refractive index of photocurable composition | Refractive Index of, photocured polymer at 810 nm | Refractive index of photocured polymer at 1550 nm |
| --- | --- | --- | --- |
| 10.3/89.7 | 1.4377 | 1.4552 | 1.4505 |
| 32.6/67.4 | 1.4349 | 1.4498 | 1.4470 |
| 49.4/50.6 | — | 1.4488 | 1.4425 |

This example shows that the diacrylates of the invention may be combined to produce a polymer of desired refractive index.

EXAMPLE 20

Preparation of a Mixture of $H_2C=CHCO_2CH_2(CF_2CFCl)_3CF_2CH_2OC(O)CH=CH_2$ and a hydrocarbon diacrylate $[(CH_3)CC_6H_4O(CH_2)_2O_2CCH=CH_2]_2$ (BDA) SR-349)

$H_2C=CHCO_2CH_2(CF_2CFCl)_3CF_2CH_2OC(O)CH=CH_2$ monomer was mixed with $[(CH_3)CC_6H_4O(CH_2)_2O_2CCH=CH_2]_2$ (ethoxylated bisphenol-A diacrylate, EBDA, Sartomer SR349) in a weight ratio of 11.2/88.8, respectively, to give a homogeneous mixture. LR 8893X (0.7 wt %) was added to this mixture as the photoinitiator. The composition was photocured according to the procedure set forth in Example 21 above. The resulting product was a clear, tough, solid polymer film. The refractive indices of the photocurable composition and the photopolymer are 1.4429(at 589 nm) and 1.4512 (at 1550 nm), respectively.

This example shows that the diacrylates of the invention may be combined with (are compatible with) other conventional hydrocarbon-based monomers.

EXAMPLE 21

Preparation of a Mixture of $H_2C=CHCO_2CH_2(CF_2CFCl)_3CF_2CH_2OC(O)CH=CH_2$ and a fluorinated diacrylate $[CH_2=CHCO_2CH_2CF(CF_3)O(CF(CF_3)CF_2O)_2CF_2CF_2]_2$ $H_2C=CHCO_2CH_2(CF_2CFCl)_3CF_2CH_2OC(O)CH=CH_2$ monomer was mixed with a highly fluorinated diaciylate, $[CH=CHCO_2CH_2CF(CF_3)O(CF(CF_3)CF_2O)_2CF_2CF_2]_2$, in a weight ratio of 70/30, respectively, to give a homogeneous mixture. LR 8893X, 0.7 wt. %, was added to this composition as photoinitiator. The composition was photocured according to the procedure set forth above. The resulting product was a clear, tough, solid polymer film. The refractive indices of the photocurable composition and the photocured polymer are 1.4092 (at 589 nm) and 1.4289 (at 633 nm), respectively. The refractive indices of the two homopolymers, $H_2C=CHCO_2CH_2(CF_2CFCl)_3CF_2CH_2OC(O)CH=CH_2$ and $[CH_2=CHCO_2CH_2CF(CF_3)O(CF(CF_3)CF_2O)_2CF_2CF_2]_2$, are 1.4435 (at 633 nm) and 1.3484 (at 633 nm), respectively.

This example shows that the diacrylates of the invention may be combined with (are compatible with) highly fluorinated monomers.

EXAMPLE 22

Preparation of a Polymer Waveguide Using a Chlorofluorinated Diacrylate of the Invention The photcurable compositions of each of Examples 14–21 is coated onto a glass substrate to a thickness of 6 to 10 μm. The coating is irradiated in a nitrogen atmosphere for 30 seconds through a quartz mask with light from a mercury-xenon arc lamp at 11.3 mW/cm². The mask is designed to produce a single-mode star coupler consisting of tapered waveguides of from 5.5 to 8.5 pm width having decreasing spacing between the guides down to 3.5 μm. Following exposure, the coating is developed by flushing with acetone from end to end to produce free-standing rib waveguides of about 5 to 9 μm width.

What is claimed is:

1. A photocurable compound of the formula:

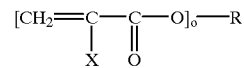

wherein o=2, X=H, R=—$CH_2R_FCH_2$—, and RF=—$(CF_2CFX_1)_aCF_2$—, and further wherein $X_1$=Cl, and a is an integer from 1 to about 10, the photocurable compound having an index of refraction between about 1.40 to 1.48.

2. The photocurable compound of claim 1 wherein a is an integer from 1 to about 7.

3. The photocurable compound of claim 1 comprising: chlorotrifluoroethylene repeating units and having at least two terminal acrylate groups.

4. The photocurable compound of claim 1 which comprises

$H_2C=CHCO_2CH_2(CF_2CFCl)_3CF_2CH_2OC(O)CH=CH_2$ and mixtures thereof.

5. A photocurable composition comprising: at least one photocurable compound according to claim 1; and at least one photoinitiator.

6. The photocurable composition of claim 5 wherein the photocurable compound is present in an amount of from about 35% to about 99.9% by weight of the photocurable composition.

7. The photocurable composition of claim 6 further comprising: at least one ethylenically unsaturated monomer, oligomer, or polymer compound.

8. The photocurable compostion of claim 7 wherein the photocurable compound and the at least one ethylenically unsaturated monomer, oligomer, or polymer compound are present in a total amount from about 35% to about 99.9% by weight of the photocurable composition, and at a weight ratio of the photocurable compound to the at least one ethylenically unsaturated monomer, oligomer, or polymer compound of from about 1:9 to about 9:1.

9. The photocurable composition of claim 5 wherein the photoinitiator is present in an amount of from about 0.01% to about 10% by weight of the photocurable composition.

10. The photocurable composition of claim 5 further comprising: one or more additives selected from the group consisting of antioxidants, photostabilizers, volume expanders, fillers, dyes, free radical scavengers, contrast enhancers, and UV absorbers.

11. The photocurable composition of claim 10 wherein the one or more additives are present in an amount from about 0.1% to about 6% by weight of the overall composition.

12. A process for producing an optical device on a substrate which comprises the steps of: applying a layer of the photocurable composition of claim 5 onto the substrate; exposing the photocurable composition to actinic radiation to form exposed areas and nonexposed areas on the substrate; and removing the nonexposed areas while leaving the exposed areas on the substrate.

13. The process of claim 12 wherein the nonexposed areas are removed with a solvent developer.

14. An optical device produced according to the process of claim 12.

15. The optical device of claim 14 which is selected from the group consisting of a waveguide, a splitter, a router, a coupler, or a combiner.

16. An optical device which comprises: a layer of the photocurable composition according to claim 5 which has been patterned and cured.

17. An optical device which comprises: a substrate; and a layer of the photocurable composition according to claim 5 disposed on the substrate, the photocurable composition being patterned and cured.

18. The optical device of claim 17 wherein the substrate is fabricated from a material selected from the group consisting of silicon, silicon oxide, or gallium arsenide.

* * * * *